(12) United States Patent
Droescher et al.

(10) Patent No.: US 6,436,917 B1
(45) Date of Patent: *Aug. 20, 2002

(54) NON-ESTROGENIC ESTRADIOL DERIVATIVE COMPOUNDS WITH ANTI-OXIDATIVE ACTIVITY

(75) Inventors: Peter Droescher, Weimar; Bernd Menzenbach, Jena; Wolfgang Roemer, Jena; Birgitt Schneider, Jena; Walter Elger, Berlin; Guenter Kaufmann, Jena, all of (DE)

(73) Assignee: Jenapharm GmbH & Co. KG, Jena (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/092,289

(22) Filed: Jun. 5, 1998

(30) Foreign Application Priority Data

Jun. 6, 1997 (DE) .......................................... 197 23 794

(51) Int. Cl.⁷ ........................ A61K 31/58; A61K 31/56; C07J 43/00; C07J 1/00; C07J 3/00
(52) U.S. Cl. ........................ 514/176; 514/182; 540/112; 540/113; 552/505; 552/610; 552/613; 552/625; 552/626; 552/627; 552/630
(58) Field of Search ................................. 540/112, 113; 552/505, 610, 613, 625, 626, 627, 630; 514/176, 182

(56) References Cited

U.S. PATENT DOCUMENTS

| | | | | | |
|---|---|---|---|---|---|
| 3,951,959 | A | * | 4/1976 | Prezewowsky et al. | 260/239.55 |
| 3,956,348 | A | * | 5/1976 | Hilscher | 260/397.5 |

FOREIGN PATENT DOCUMENTS

| | | | |
|---|---|---|---|
| CA | 2176368 | * | 5/1995 |
| DE | 43 38 314 C1 | | 3/1995 |
| DE | 43 38 316 A1 | | 5/1995 |

OTHER PUBLICATIONS

CAS printout of Payne et al., Differential Effects of Estrogens in Tissues: a Comparison of Estrogen Receptor in Rabbit Uterus and Vigina, Endocrinology, vol. 106, No. 5, pp. 1345–1352, 1980.*
CAS printout of Cambie et al., Aromatic Steroids. V. Chromium Trioxide Oxidation Products of Some Aromatic Steroids, New Zealand Journal of Science, vol. 15, No. 2, pp. 182–199, 1972.*
Christman et al., Relationship Between Estrogen Structure and Conformational Changes in Estrogen Receptor/DNA Complexes, J. Steroid Biochem. Molec. Biol., vol. 54, No. 5/6, pp. 201–210, Sep. 1995.*
Tinant et al., Crystal Structure of 1,3,5(10)–Estratriene–1, 17.beta.–diol 17–Acetate, Bull. Soc. Chim. Belg., vol. 101, No. 9, pp. 771–774, Sep. 1992.*
Zydowsky et al., Preparation and Acid–catalysed Rearrangements of a Steroidal 1,4–Quinol, J. Chem. Soc. Perkin Trans I, No. 8, pp. 1679–1681, 1980.*
Takeda et al., Preparation of the Steroidal 1,4, 11–Trien–3–ones and a Surprisingly Rapid Dienone–phenol Rearrangement, Chem. Pharm. Bull., vol. 23, No. 11, pp. 2711–2727, Nov. 1975.*
Nambara et al., Synthesis of 1,2– and 2,3–Dimethoxy–4–methylestratrienes, Chem. Pharm. Bull., vol. 20, No. 2, pp. 336–342, 1972.*
Piatak et al., Cerium(IV) Oxidation of 4–Methyl estra–1,3, 5(10)–trienes, J. Chem. Soc. D., No. 14, p. 772, Jul. 1971.*
Liston et al., The Enol Acetylation of Alkylated .delta.–3–Oxo Steroids. A Novel Enone–Phenol Transformation, Journal of Organic Chemistry, vol. 34, No. 8, pp. 2288–2296, Aug. 1969.*
Cambie et al., Aromatic Steroids. Part II. Chromium Trioxide Oxidation of Some Oestra,1,3,5(10)–trienes, J. Chem. Soc. (C), No. 9, pp. 1234–1240, 1969.*
Rodig et al., Studies on the Synthesis of Enol Acetates of the .delta.–3–Keto AB–trans Steroid System, Journal of Organic Chemistry, vol. 32, No. 5, pp. 1423–1427, May 1967.*
M.J. Reed et al., Steroid Sulphatase Inhibitor . . . , Drugs Future 19, 1994, p. 673.
W. Elger, et al., "Sulfamates of Various Estrogens . . . " J. Steroid Biochem. Bio 55, 1995, pp. 395–403.
Dorfman,R.J., (HRSG) Methods in Hormone Research: Academic Press New York, 1969, p. 72FF.
Braughler,J.M. "The Aminosteroids: Potent Inhibitors . . . " Drugs Futures 14, 1989, pp. 141–152.
Buege,A. et al, Microsomal Lipid Peroxidation, Methods Enzymology, 1978, pp. 302–310.
Ruiz–Larrea B. et al, "Antioxidant Effects of Estradiol . . . " Steroids 60, 1994, pp. 383–388.
Fisher M. et al "A 21–Aminosteroid Inhibits Oxidation . . . " Atherosclurosis 90, 1991 pp. 197–202.
Leake, D.S. and Rankin S.M., "the Oxidative Modification of . . . " biochem J. 270, 1990, pp. 741–748.
Laihia,J.K. rt al, "Lucigenin and Linoleate Enhanced . . . " Free Rad. Biol. Med. 14, 1993, pp. 457–461.
Ruiz–Larrea et al: "Effects of Estrogen on the Redox Chemistry of Iron...", Steroids 60, 1995, pp. 780–783.

* cited by examiner

*Primary Examiner*—Brenda Coleman
(74) *Attorney, Agent, or Firm*—Michael J. Striker

(57) ABSTRACT

New non-estrogenic derivative compounds of estradiol, which have no estrogenic activity and comparatively high anti-oxidative activity, are disclosed. These new non-estrogenic derivative compounds are potentially useful as non-estrogenic antioxidants, especially for administration in post-menopausal women and in men. The compounds of the invention can also inhibit aromatase and sulfatase.

5 Claims, No Drawings

NON-ESTROGENIC ESTRADIOL DERIVATIVE COMPOUNDS WITH ANTI-OXIDATIVE ACTIVITY

BACKGROUND OF THE INVENTION

The present invention relates to new non-estrogenic derivative compounds of estradiol with antioxidative activity.

It is known from the patent literature, namely from DE 43 38 314 C1, that estradiol and its known derivatives with phenolic A-rings and 17-hydroxy groups have fundamental antioxidative activity. These substances have a more or less strong binding affinity to estrogen receptor sites according to their structure. The high affinity of natural 17β-estradiols (100%) is usually considerably decreased by structural changes, such as isomerization or derivativization. However it still amounts to 23% for 17α-estradiol and it is still 8.6% for the enantiomer of the natural estradiol, 8α, 9β, 14β-estra-1,3,5(10)-trien-3,17α-diol (ent-estradiol). These values are not always tolerable depending on the dosage and application duration during administration of the substances with the aim to increase the body's antioxidative capacity.

When a large substituent is introduced at the 17-carbon atom according to German Patent Document DE 43 38 316 A1, for example in 17α-4'-dimethylamino-phenylmethyl-estra-1,3,5(10),9(11)-tetraen-3,17-diol, the binding affinity can be reduced up to less than 1% while increasing the antioxidative activity. However in vivo a high estrogen activity was found for the corresponding 3-methyl ether, 3-methoxy-17α-4'-dimethylamino-phenylmethyl-estra-1,3,5(10)-trien-17-ol.

SUMMARY OF THE INVENTION

It is an object of the present invention to provide new estradiol derivative compounds with antioxidative activity having no estrogenic activity.

According to the invention, the non-estrogenic estradiol derivative compounds with antioxidative activity include the compounds of the following formula (I):

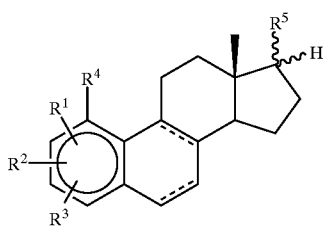

I wherein $R^1$ is H or OH, $R^2$ and $R^3$ are the same or different and are each, independently of each other, H or $CH_3$, $R^4$ and $R^5$ are the same or different and are each, independently of each other, —OH, —O(CO)$R^6$, —OR$^6$ or —OSO$_2$NR$^7$R$^8$, wherein $R^6$ represents an aryl group or an alkyl group having 1 to 4 carbon atoms, and the $R^7$ and $R^8$ groups are each, independently of each other, H or an alkyl group having one to four carbon atoms, or $R^7$ and $R^8$ together with the N atom represent a polymethylenimino group with 4 to 6 carbon atoms or a morpholino group, each of the dashed lines represents either an additional bond or not in the ring positions indicated by the respective dashed lines so that either a double bond or a single bond is present at the respective ring positions; but with the proviso that the compounds of formula I do not include 4-methyl-estra-1,3,5(10)-trien-1,17β-diol; and the non-estrogenic estradiol derivative compounds with antioxidative activity also include the compounds of the following formula (II):

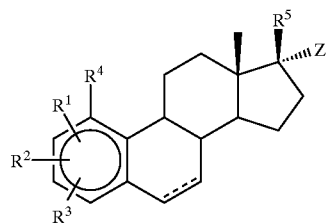

II wherein $R^1$ is H or OH, $R^2$ and $R^3$ are the same or different and are each, independently of each other, H or $CH_3$, Z is an unsubstituted group represented by $(CH_2)_n$APh, wherein Ph represents a phenyl group and A represents a bond for n=0 or a bond, O, S or Se for n=1, or Z is a 17α-substituent group containing a phenyl group, Ph, having from 1 to 2 hydroxy group substituents and 0 to 2 methyl group substituents or a dimethylaminophenyl group and 0 to 2 methyl group substituents;

$R^4$ and $R^5$ are the same or different and are each, independently of each other, —OH, —O(CO)$R^6$, —OR$^6$ or —OSO$_2$NR$^7$R$^8$, wherein $R^6$ represents aryl group or an alkyl group having 1 to 4 carbon atoms, and the $R^7$ and $R^8$ groups are each, independently of each other, H or an alkyl group having one to four carbon atoms, or $R^7$ and $R^8$ together with the N atom represent a polymethylenimino group with 4 to 6 carbon atoms or a morpholino group, and each of the dashed lines represents either an additional bond or not in the ring positions indicated by the respective dashed lines so that either a double bond or a single bond is present at the respective ring positions.

The preferred compounds of the invention are:
4-methyl-estra-1,3,5(10)-trien-1,17α-diol,
4-methyl-estra-1,3,5(10),6-tetraen-1,17α-diol,
4-methyl-estra-1,3,5(10),6-tetraen-1,17β-diol,
4-methyl-estra-1,3,5(10),6,8-pentaen-1,17β-diol,
4-methyl-estra-1,3,5(10),6,8-pentaen-1,17α-diol,
17α-4'-hydroxyphenylmethyl-4-methyl-estra-1,3,5(10)-trien-1,17β-diol,
17α-4'-hydroxy-phenoxymethyl-4-methyl-estra-1,3,5(10)-trien-1,17β-diol,
17α-4'-hydroxy-thiophenoxymethyl-4-methyl-estra-1,3,5(10)-trien-1,17β-diol,
17α-4'-dimethylamino-phenylmethyl-4-methyl-estra-1,3,5(10)-trien-1,17β-diol,
17α-3',5'-dimethyl-4'-hydroxy-phenylmethyl-4-methyl-estra-1,3,5(10)-trien-1,17β-diol.
17α-3',5'-dimethyl-4'-hydroxy-phenylmethyl-4-methyl-estra-1,3,5(10),6-tetraen-1,17β-diol and
17α-4'-hydroxy-phenoxymethyl-4-methyl-estra-1,3,5(10),6-tetraen-1,17β-diol.

It was surprisingly found that these compounds, regioisomers of estradiol and their derivatives, which have a phenolic hydroxy group on carbon atom 1 and a hydroxy group on carbon atom 17, are neither estrogens in vitro nor in vivo, as shown in Tables 1 and 2. At the same time these compounds have an antioxidative activity that is clearly increased in comparison to estradiol—as demonstrated in Tables 3 and 4.

Since the substances have an intact steroid framework and a polarizability comparable to the natural estrogens, it is expected that the ability to penetrate the blood-brain barrier and for membrane-receptor exchange remain the same as in the natural estrogens.

The estradiol derivative compounds according to the invention, in which the estrogeneity is practically completely eliminated while improving the antioxidative activity, are potentially suitable for use as non-estrogenic antioxidants, especially for administration to postmenopausal women and in men. The absence of estrogen action is also advantageous when the inhibition of enzymes generating estrogens is the aim of a therapeutic strategy, especially the inhibition of aromatase and sulfatase. The enzymes, aromatase and sulfatase, release estrone from estrone sulfate. A strong inhibition of sulfatase by sulfamates of the currently known phenolic steroids according to M. J. Reed, et al, "Steroid Sulphatase Inhibitor: A new endrocrine therapy", Drugs Future 19 (1994), p. 673, and W. Elger, et al, "Sulfamates of various estrogens are prodrugs with increased systemic and reduced hepatic estrogenicity at oral application", J. Steroid Biochem. Biol., 55, (1995), p. 395 to 403. This leads to inhibition of release of estrone from estrone sulfate in vitro and in vivo. The compounds according to the invention are thus also potential inhibitors of aromatase and sulfatase.

The measured estrogen-receptor binding of the compounds according to the invention, which is a measure of their estrogenicity or estrogen action, is set forth in the following Table I.

For comparison to the compounds according to the invention 17β-estradiol, 17α-estradiol, ent-17β-estradiol (J 855), 3-methoxy-17α-4'-dimethylamino-phenylmethyl-estra-1,3,5(10)-trien-17-ol (J 848) and 17α-4'-dimethylamino-phenylmethyl-estra-1,3,5(10),9(11)-tetraen-3,17-diol (J 844), are similarly shown in Table I and indicated with an "x".

TABLE I

RELATIVE BINDING AFFINITY OF SELECTED COMPOUNDS TO ESTROGEN RECEPTOR SITES

| Compounds | | relative binding affinity (% binding to estrogen receptor). |
|---|---|---|
| 17β-estradiol | (x) | 100.0 |
| 17α-estradiol | (x) | 22.8 |
| ent-17β-estradiol - - - J 855 | (x) | 8.6 |
| 4-methyl-estra-1,3,5(10)-trien-1,17β-diol -J1178 | | 0.04 |
| 4-methyl-estra-1,3,5(10)-trien-1,17α-diol -J1179 | | <0.03 |
| 3-methoxy-17α-4'-dimethylamino-phenylmethyl-estra-1,3,5(10)-trien-17-ol-J 848 | (x) | 0.7 |
| 17α-4'-dimethylamino-phenylmethyl-estra-1,3,5(10),9(11)-tetraen-3,17-diol-J 844 | (x) | 0.7 |

The non-estrogenic activity of the compounds of the invention in vitro is apparent from the comparison to the references substances in Table I.

Estrogenicity or estrogen activity is further demonstrated for select compounds with the aid of the in vivo results according to the Allen-Doisy Test. These results appear in the following Table II.

Table II shows the results of the estrogenicity test in vivo in ovariectomized rats. Estrogens lead to characteristic changes in vaginal epithelium in ovariectomized rodents. The upper cells become heavily cornified and a strong proliferation occurs. These changes in cell formation were determined by vaginal smears. The occurrence of cornified anuclear epithelial cells is an expression of estrogen-specific activity (Allen-Doisy Test).

For comparison to the compounds according to the invention 17β-estradiol, 17α-estradiol, ent-17β-estradiol (J 855) and 3-methoxy-17α-4'-dimethylamino-phenylmethyl-estra-1,3,5(10)-trien-17-ol (J 848), are similarly shown in Table II and indicated with an "x".

TABLE II

ESTROGEN ACTIVITY RESULTS FOR SELECTED COMPOUNDS
Allen-Doisy Test, one-time subcutaneous administration d1;
flaking, d1–d4 vaginal scale stage 3(reagent/group)

| Substance | Dosage, μg/animal | | | | | | | | | | | | |
|---|---|---|---|---|---|---|---|---|---|---|---|---|---|
| | 0 | 0.03 | 0.1 | 0.3 | 1 | 3 | 10 | 30 | 100 | 300 | 1000 | 3000 | 10000 |
| OVX-contr. | 0/5 | | | | | | | | | | | | |
| 17α-E2 (x) | | | | | | | 0/6 | 6/6 | | | | | |
| 17β-E2 (x) | | 1/5 | 5/5 | | | | | | | | | | |
| J 855 (x) | | | | | | | | | | | 5/5 | | 5/5 |
| J 1178 | | | | | | | | | | | 0/5 | | 1/5 |
| J 1179 | | | | | | | | | | | | | 0/5 |
| J 848 (x) | | | | | | | 0/5 | | 2/5 | | | | |

It is apparent from Table II that the compounds according to the invention display no estrogen activity in comparison to the reference substances, even at high dosages.

The antioxidative activity of the compounds according to the invention is demonstrated by means of evidence of iron-(II)-sulfate-catalyzed lipid peroxidation inhibition in Synaptosomal membrane fractions (rat). This evidence is set forth in Table III.

The lipid peroxidation inhibitory action of the respective compounds is characterized by the $IC_{50}$ inhibition value. The $IC_{50}$ is the amount of the added substance which produces a 50% inhibition of lipid peroxidation. (Table III).

For comparison to the compounds according to the invention, the $IC_{50}$ of 17β-estradiol, 17α-estradiol, α-tocopherol (Vitamin E) and butyrohydroxytoluene (BHT) were also measured as standards and are similarly shown in Table III, indicated with an "x".

TABLE III

IRON-(II)-SULFATE-CATALYZED LIPID PEROXIDATION INHIBITION OF SELECTED COMPOUNDS

| COMPOUND | | LIPID PEROX-IDATION INHIBITION ($IC_{50}$ μMol/l) |
|---|---|---|
| 17β-estradiol | (x) | 12.40 |
| 17α-estradiol | (x) | 8.9 |
| α-tocopherol (Vitamin E) | (x) | 117.0 |
| 4-methyl-estra-1,3,5 (10)-trien-1,17β-diol -J1178 | | 1.7 |
| 4-methyl-estra-1,3,5(10)-trien-1,17α-diol -J117.9 | | 1.94 |
| butyrohydroxytoluene (BHT) | (x) | 0.95 |

Table III clearly shows that natural estrogens effectively inhibit the formation of thiobarbituric acid reactive substances (TBARS) in lipid peroxidation processes induced with Fenton's reagent. Accordingly the natural antioxidatively acting estrogens, 17α-estradiol and 17β-estradiol, already have the ability to suppress lipid peroxidation in Synaptosomal membrane/lipid fractions and consequently to maintain the balance of different redox processes. However the isomeric compounds of the invention, 4-methyl-estra-1,3,5(10)-trien-1,17β-diol and 4-methyl-estra-1,3,5(10)-trien-1,17α-diol, have considerably stronger antioxidative action.

The antioxidative activity of the compounds according to the invention is further evidenced by the inhibition of the Fe(II)-autooxidation and stimulation of Fe(III) reduction, as shown in Table IV.

For comparison to the compounds according to the invention, measured inhibition results of 17β-estradiol, 17α-estradiol and catechol estrogens are similar shown in Table IV, indicated with an "x".

TABLE IV

INHIBITION OF FE(II)-AUTOOXIDATION AND STIMULATION OF FE(III) REDUCTION OF SELECTED COMPOUNDS

| COMPOUND | | FE(II)-AUTOXIDATION Inhibition, % | FE(III)-REDUCTION Stimulation, % |
|---|---|---|---|
| 17β-estradiol | (x) | ≦1 | ≦1 |
| 17α-estradiol | (x) | ≦1 | ≦1 |
| 2-hydroxy-17β-estradiol | (x) | 64.20 | 35.26 |
| 4-hydroxy-17α-estradiol | (x) | 59.51 | 32.71 |
| 4-methyl-estra-1,3,5(10)-trien-1,17β-diol (J1178) | | 22.26 | 19.23 |
| 4-methyl-estra-1,3,5(10)-trien,-1,17α-diol (J1179) | | 26.07 | 21.41 |

Table IV shows that the "classical" estrogens, 17β-estradiol and 17α-estradiol, do not or do not substantial change the tested Fe(II)-autooxidation process. In comparison the compounds according to the invention, 4-methyl-estra-1,3,5(10)-trien-1,17β-diol (J1178) and 4-methyl-estra-1,3,5(10)-trien-1,17α-diol (J1179), have the ability to inhibit the Fe(II)-autooxidation process. Furthermore it is also apparent that the stimulation of the Fe(III)-reduction to Fe(II) occurs and is correlated with the Fe(II) autooxidation results. The comparison with the catechol estrogens with the inhibitory action of about 60% shows that the compounds of the invention, 4-methyl-estra-1,3,5(10)-trien-1,17β-diol (J1178) and 4-methyl-estra-1,3,5(10)-trien-1,17α-diol (J1179), have good antioxidative action.

A substantially higher antioxidative activity was reported in the following models for the compounds of the invention in comparison to that of the natural estrogens, 17β-estradiol and 17α-estradiol:

inhibition of the up-take of oxidatively-modified LDL cholesterol in macrophages, and inhibition of the formation of superoxide anion radicals.

BIOLOGICAL TESTING METHODS FOR ESTROGENS AND ANTIOXIDATIVE ACTIVITY OF THE COMPOUNDS ACCORDING TO THE INVENTION

Allen-Doisy Test

Purpose

Subcutaneous Testing for Estrogen Activity

Principle

Estrogens lead to characteristic changes in vaginal epithelium with ovariectomized rodents. Strong proliferation and cornification of the upper cell layer occurs. These changes are detectable in cells from vaginal smears. The occurrence of cornified anuclear epithelial cells is an expression of an estrogen-specific activity—i.e. the Allen-Doisy Test—according to R. J. Dorfman, (Hrsg.), Methods in Hormone Research, p. 72 ff, Academic Press, New York, 1969.

Animals

White Wistar Rats (origin: Shoe: WIST=Mol : WIST, n=48) that weighed from 180 to 200 g were supplied, divided randomly into trial groups (n=3 to 5 animals/group), habituated in supporting conditions for about one week and subsequently ovariectomized under anesthesia with ursotami.

Habitat: Makrolon® cage, type M IV, with controlled illumination (12 hours light/12 hours darkness).

Food: Standard diet for rats and mice; drinking water ad libitum.

Formulation and Administration of Test Substances

The test substances for subcutaneous and oral administration were formulated in benzyl benzoate/castor oil (1+4)

or in polyoxyethylene(50-stearate) by Myrj® (85 mg polyoxyethylene(50-stearate) in 100 ml 0.9% w/v sodium chloride solution).

The administered volume amounted to 0.2 ml/animal.

After weighing the respective test substance was dissolved in benzyl benzoate by treatment in an ultrasonic bath (30 minutes at about 60° C. water temperature) and subsequently the appropriate amount of castor oil was added; or After the weighing the respective test substance was suspended in polyoxyethylene(50-stearate) by Myrj® (with addition of a small amount of zirconium spheroids) by treatment in an ultrasonic bath (30 minutes at about 60° C. water temperature).

Experimental Procedure

Rats with a weight of about 200 g were ovariectomized under anesthesia with ursotami and about 2 weeks after that the animal was tested in the presence of a castrated vaginal cell formation (dioestrus). After that 0.2 ml per animal of the test substance was administered once subcutaneously. Vaginal smears were taken 24, 48, 54 and 72 hours after the one-time administration of the test substance and subsequent oestrus stages were evaluated(dioestrus=1; proestrus=2; oestrus=3; metoestrus=4). The experiment was ended after four days according to the standard ALLEN-DOISY test. The animals were sacrificed under anesthesia in ether by dislocation of the neck vertebral column, the uterus was prepared and its moist weight (without secretion) was measured. The suprarenal capsules were also prepared and weighed.

Analysis

The results of the colpotropic test—the occurrences of oestral vaginal cell forms as reagents per doses group and the uteropic activity(uterus weight) were measured. The average of the uterus weight of the test groups was compared with the average of the vehicular groups and, if necessary, the significance of the differences was determined by a t-test according to STUDENT. The moist weight of the suprarenal capsules of all groups was also determined.

Iron (II) Sulfate-catalyzed Lipid Peroxidation Inhibition in Synaptosomal Membrane Practions (Rats)

Materials and Methods

The testing of the ability of the substances according to the invention to inhibit lipid peroxidation was performed according to J. M. Braughler, et al, "The 21-aminosteroids: Potent inhibitors of lipid peroxidation for the treatment of central nervous system trauma and ischemia", Drugs Future 14, pp. 141 to 152 and according to A. Buege, et al, "Microsomal Lipid Peroxidation", Methods of Enzymology 52 (1978), p. 302 to 310, by means of the malondialdehyde/thiobarbituric acid assays:

Materials

17β-estradiol (Jenapharm GmbH), 17α-estradiol (Sigma Chemicals), α-tocopherol (Sigma Chemicals), thiobarbituric acid (TBA; Fluka), Iron (II) sulfate (Serva). All other biochemicals are of the highest analytical purity grade.

Reaction starting Material

The 1 ml biological sample (contains 0.1 mg plasma membranes) includes Fenton's Reagent and Drug. The 1 ml total volume is divided in the following manner: 0.01 ml Synaptosomal membrane fraction; 0.1 ml iron(II) sulfate (2 mM); 0.1 ml hydrogen peroxide (2 mM); up to 0.5 ml test substance solution and a proportionate amount of 0.9% NaCl solution (not PBS) to fill to 1 ml total volume. The reaction starting material with and without the test substances also contains 10% ethanol (total) as vehicle for the test substance.

Procedure

The reaction starting material is incubated for 30 min at 37° C., subsequently stopped with 2 ml of reagent A and incubated for 10 minutes at constant 80° C. After cooling in an ice bath (10 min) the sample is centrifuged (1,000×g; 4° C.). The supernatant (stable up to 2 hours) is measured at 535 nm against a blind value, which contains all the reagents up to the membrane fraction. A reaction starting material that contains Fenton's Reagent and the 10% ethanol as vehicle besides the membrane fraction operates as a comparative sample.

Composition of the Reagent A:

15% (w/v) trichloroacetic acid (15 g); 0.375% (w/v) thiobarbituric acid (375 mg); 0.25 N HCl (2.11 ml conc. HCl) in 100 ml aqueous solution. The test substances were introduced preferably into 95% ethanol in the form of a 20 millimolar original solution (kept at −20° C., stable over at time interval of 3 months) and diluted immediately prior to the beginning of the experiment. The testing takes place in a dosage range of 0.1 to 150 $\mu$M. A suitable standard substance is introduced in all experimental samples.

Analysis Parameter

Dosage effectiveness analysis of the test and standard substances.

Measurement of the lipid peroxidation inhibition values with at least five substance concentrations in an inhibition range of 30 to 70%, in relation to the test value for the vehicle (advantageously ethanol) and without the substance effect.

The results for the substances are reported as $IC_{50}$-values (micromolar test concentrations at 50% inhibition of iron (II) catalyzed lipid peroxidation).

Inhibition of Fe(II) Autooxidation and Stimulation of Fe(III) Reduction

1. Fe(II) Oxidation Assay Material and Methods

The testing of the substances for Fe(II)-autooxidation inhibition activity occurs according to B. Ruiz-Larrea, et al, "Antioxidant effects of estradiol and 2-hydroxyestradiol on iron-induced lipid peroxidation of rat liver microsomes", Steroids 39 (1994), pp. 383–388 and B. Ruiz-Larrea, et al, Effects of estrogens on the redox chemistry of iron: "A possible mechanism of the antioxidant action of estrogens", Steroids 60 (1995), pp. 780–783.

All autooxidation experiments involving the Fe(II) ions were performed in aqueous solutions, which contain synaptosomal membrane/lipid fractions. A 1.0 ml biological sample containing 50 $\mu$M Fe(II) sulfate, 45 mM tris-HCl buffer (pH=7.4) and 0.08 mg of synaptosomal proteins were incubated with test substances dissolved in ethanol (10% v/v) for 10 min in a water bath at 37° C., subsequently stopped by addition of 50 $\mu$L of a 0.32 M 1,10-phenanthrolene solution and the extinction of Fe(II) phenanthroline complexes at 510 nm was measured.

Materials

17β-estradiol (Jenapharm GmbH), 17α-estradiol (Sigma Chemicals), 2-hydroxy-17β-estradiol and 4-hydroxy-17α-estradiol (TBA; Fluka), Iron (II) sulfate (Serva).

All other biochemicals are of the highest analytical grade of purity. The test substances are preferably made in the form of a 20 millimolar stock solution in 95% ethanol and diluted immediately prior to the start of the experiment. The experiment is performed in a dosage range of 0.1 to 150 $\mu$M.

A suitable standard substance is used in all experiments.

Analysis Parameter

Dosage effectiveness analysis of the test and standard substances.

2. Fe(III) Reduction Assay

The testing of the substances for their ability to stimulate Fe(III) reduction occurs according to B. Ruiz Larrea, et al, "Antioxidant effects of estradiol and 2-hydroxyestradiol on iron-induced lipid peroxidation of rat liver microsomes", Steroids 39 (1994), p. 383–388 and B. Ruiz-Larrea, et al, Effects of estrogens on the redox chemistry of iron: A possible mechanism of the antioxidant action of estrogens", Steroids 60 (1995), pp. 780 to 783.

The biological sample contained the following components: 25 μM Fe(III) chloride in 150 mM tris-HCl (pH=7.4), 15 mM 1,10-phenanthrolene and the substance to be tested, dissolved in an ethanol vehicle. The formation of the Fe(II) phenanthroline complex is registered spectrophotometrically at 510 nm.

Inhibition of the Up-take of Oxidatively-modified LDL Cholesterol in Macrophages The measurement of the up-take of oxidatively-modified LDL cholesterol in murine macrophages and blood macrophages of human origin was made by the cell culture methods according to M. Fischer, et al, "A 21-aminosteroid inhibits oxidation of human low density lipoprotein by human monocytes and copper" Athersclerosis 90 (1991), pp. 197–202 or according to D. S. Leake and S. M. Rankin, "The oxidation modification of low-density lipoproteins by macrophages", J. Biochem. 270 (1990), pp. 741 to 748.

Inhibition of Superoxide Anion Radical Formation

The measurement of the xanthine oxidase inhibitory action was performed using linoleic acid as the forming agent for the superoxide anion radical by means of a lucigen/luminol-amplified xanthine/xanthine oxidase-dependent chemiluminescence reaction according to J. K. Laihia, et al, "Lucigen and linoleate-enhanced chemiluminescent assay for superoxide dismutase activity", Free Radical Biological Medicine 14 (1993), pp. 457 to 461.

The disclosure in German Patent Application 197 23 794.0 of Jun. 6, 1997 is incorporated here by reference. This German Patent Application discloses the invention, which is described hereinabove and claimed in the claims appended hereininbelow, and provides the basis for a claim of priority for the instant invention under 35 U.S.C. 119.

While the invention has been illustrated and described as embodied in a non-estrogenic estradiol derivative compounds with anti-oxidative activity, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

We claim:
1. A non-estrogenic estradiol compound with antioxidative activity of the formula I:

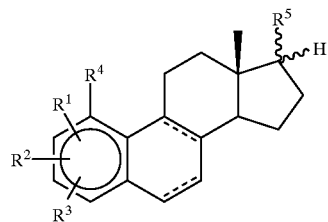

I wherein $R^1$ is H or OH,
$R^2$ and $R^3$ are the same or different and are each, independently of each other, H or $CH_3$,
$R^4$ and $R^5$ are the same or different and are each, independently of each other, —OH, —O(CO)$R^6$, —OR$^6$ or —OSO$_2$NR$^7$R$^8$, wherein R$^6$ represents an alkyl group having 1 to 4 carbon atoms, and the R$^7$ and R$^8$ groups are each, independently of each other, H or an alkyl group having one to four carbon atoms, or R$^7$ and R$^8$ together with the N atom represent a polymethylenimino group with 4 to 6 carbon atoms or a morpholino group,
each of the dashed lines represent either an additional bond or not in the ring positions indicated by the respective dashed lines so that either a double bond or a single bond is present at said ring positions; and
wherein $R^5$ is a 17α group.

2. A non-estrogenic estradiol compound with antioxidative activity of the formula II:

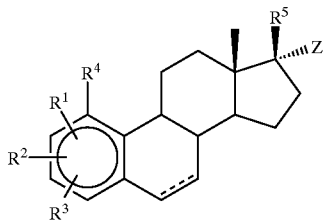

II wherein $R^1$ is H or OH,
$R^2$ and $R^3$ are the same or different and are each, independently of each other, H or $CH_3$,
Z is an unsubstituted group represented by —(CH$_2$)$_n$APh, wherein Ph represents an unsubstituted phenyl group or a substituted phenyl group and A represents a bond for n=0 or a bond, O, S or Se for n=1, said substituted phenyl group having from 1 to 2 hydroxy group substituents and 0 to 2 methyl group substituents or a dimethylaminophenyl group and 0 to 2 methyl group substituents;
$R^4$ and $R^5$ are the same or different and are each, independently of each other, —OH, —O(CO)$R^6$, —OR$^6$ or —OSO$_2$NR$^7$R$^8$, wherein R$^6$ represents an aryl group or an alkyl group having 1 to 4 carbon atoms, and the R$^7$ and R$^8$ groups are each, independently of each other, H or an alkyl group having one to four carbon atoms, or R$^7$ and R$^8$ together with the N atom represent a polymethylenimino group with 4 to 6 carbon atoms or a morpholino group, and each of the dashed lines represent either an additional bond or not in the ring positions indicated by the respective dashed lines so that either a double bond or a single bond is present at said ring positions.

3. A non-estrogenic estradiol compound selected from the group consisting of 4-methylestra-1,3,5(10)-trien-1,17α-diol 4-methylestra-1,3,5(10),6-tetraen-1,17α-diol.

4. 4-methylestra-1,3,5(10)-trien-1,17α-diol.

5. A non-estrogenic estradiol compound selected from the group consisting of 4-methylestra-1,3,5(10),6-tetraen-1,17β-diol, 4-methylestra-1,3,5(10),6,8-pentaen-1,17β-diol, 17α-4'-hydroxyphenylmethyl-4-methylestra-1,3,5(10)-trien-1,17β-diol, 17α-4'-hydroxyphenoxymethyl-4-methylestra-1,3,5(10)-trien-1,17β-diol, 17α-4'-hydroxythiophenoxymethyl-4-methylestra-1,3,5(10)-trien-1,17β-diol, 17α-4'-dimethylaminophenylmethyl-4-methylestra-1,3,5(10)-trien-1,17β-diol, 17α-3',5'-dimethyl-4'-hydroxy-phenylmethyl-4-methylestra-1,3,5(10 )-trien-1, 17β-diol, 17α-3',5'-dimethyl-4'-hydroxy-phenylmethyl-4-methylestra-1,3,5(10), 6-tetraen-1,17β-diol and 17α-4'-hydroxy-phenoxymethyl-4-methylestra-1,3,5(10),6-tetraen-1,17β-diol.

* * * * *